United States Patent [19]
Doria et al.

[11] Patent Number: 5,166,152
[45] Date of Patent: Nov. 24, 1992

[54] TRICYCLIC 3-OXO-PROPANENITRILE DERIVATIVES

[75] Inventors: Gianfederico Doria; Anna M. Isetta; Mario Ferrari, all of Milan; Domenico Trizio, Cassina Rizzardi, all of Italy

[73] Assignee: Farmitalia Carlo Erba SRL, Italy

[21] Appl. No.: 635,158

[22] PCT Filed: Jun. 20, 1989

[86] PCT No.: PCT/EP89/00683
§ 371 Date: Dec. 20, 1990
§ 102(e) Date: Dec. 20, 1990

[87] PCT Pub. No.: WO89/12638
PCT Pub. Date: Dec. 28, 1989

[30] Foreign Application Priority Data

Jun. 20, 1988 [GB] United Kingdom ............... 8814586

[51] Int. Cl.$^5$ ............... A61K 31/535; A61K 31/445; C07D 231/54; C07D 211/08
[52] U.S. Cl. ............... 514/228.5; 514/232.8; 514/318; 514/253; 514/322; 514/339; 514/406; 544/60; 544/140; 544/371; 544/131; 544/364; 546/194; 546/199; 546/271; 548/359.5
[58] Field of Search ............... 544/140, 60, 371; 548/370; 514/232.8, 228.5, 253, 322, 339, 406; 546/199, 271

[56] References Cited

U.S. PATENT DOCUMENTS

| | | | |
|---|---|---|---|
| 3,679,699 | 7/1972 | Oppolzer | 260/310 |
| 4,268,516 | 5/1981 | Lombardino et al. | 424/273 |
| 4,816,467 | 3/1989 | Doria et al. | 548/370 |

FOREIGN PATENT DOCUMENTS

| | | |
|---|---|---|
| 0274443 | 7/1988 | European Pat. Off. . |
| 0286346 | 10/1988 | European Pat. Off. . |
| 1926023 | 11/1969 | Fed. Rep. of Germany . |
| 2227741 | 8/1990 | United Kingdom . |

*Primary Examiner*—Mary C. Lee
*Assistant Examiner*—Mary Susan H. Gabilan

[57] ABSTRACT

Compounds having the general formula (I)

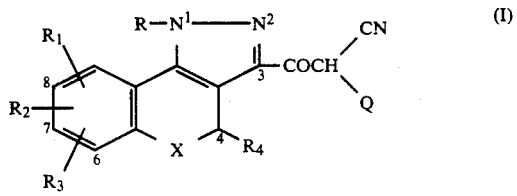

wherein
X represents an oxygen atom or a $-S(O)_n-$ group, wherein n is zero, 1 or 2;
R represents $C_1-C_6$ alkyl, pyridyl or substituted or unsubstituted phenyl;
$R_2$, $R_3$ and $R_4$ are as defined herein; and Q represents hydrogen, carboxy, $C_2-C_7$ alkoxycarbonyl or a $-CON(R_a)'R_b$ group wherein $R_a$ and $R_b$ are as defined herein; and their pharmaceutically acceptable salts have immunomodulating activity and are useful in particular as immunostimulating agents, in the treatment of neoplastic diseases and acute and chronic infections of both bacterial and viral origin in mammals.

6 Claims, No Drawings

TRICYCLIC 3-OXO-PROPANENITRILE DERIVATIVES

The present invention relates to tricyclic 3-oxo-propanenitrile derivatives, to a process for their preparation and to pharmaceutical compositions containing them.

The compounds of the invention have the general formula (I)

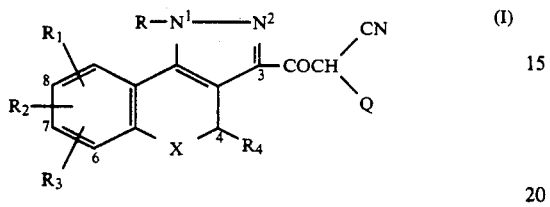

wherein
X represents an oxygen atom or a —S(O)$_n$— group, where n is zero, 1 or 2;
R represents $C_1$–$C_6$ alkyl, pyridyl or phenyl, the phenyl being unsubstituted or substituted by one or two substituents chosen independently from halogen, trifluoromethyl, $C_1$–$C_6$ alkyl, $C_1$–$C_6$ alkoxy, nitro, amino, formylamino and $C_2$–$C_8$ alkanoylamino;
$R_1$ is
a°) hydrogen, di($C_1$–$C_6$ alkyl)-amino or a

group wherein R' and R", the same or different, is $C_1$–$C_6$ alkyl or R' and R", taken together with the nitrogen atom to which they are linked, form a heterocyclic ring which is selected from N-pyrrolidinyl, N-piperazinyl, hexahydroazepin-1-yl, thiomorpholino, morpholino and piperidino and which is unsubstituted or substituted by $C_1$–$C_6$ alkyl;
b°) $CH_2OH$, CHO, COOH or $C_2$–$C_7$ alkoxycarbonyl;
c°) a

group wherein $R_d$ is hydrogen or $C_1$–$C_6$ alkyl and $R_c$ is hydrogen, phenyl or the side-chain of an α-aminoacid;
d°) a

group, wherein $R_c$ is as defined above;
e°) a

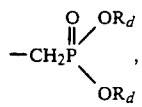

a —$CH_2OCO(CH_2)_nCOOR_d$ or a —NH-$CO(CH_2)_nCOOR_d$ group wherein n and $R_d$ are as defined above;
f°) a —CH=N—OR'$_1$ group wherein R'$_1$ is hydrogen or a —$CH_2COOH$ group;
g°) a —CH=N—NH—R'$_2$ group wherein R'$_2$ is hydrogen, —$CH_2CH_2OH$, $C_2$ or $C_3$ alkoxycarbonyl or a —$(CH_2)_p$—R'$_3$ group wherein p is 1 or 2 and R'$_3$ is COOH or $C_2$–$C_7$ alkoxycarbonyl;
H°) a

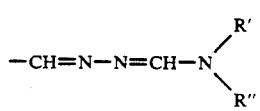

group wherein R' and R" are as defined above; or
k°) a

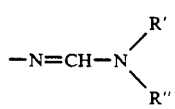

group wherein R' and R" are as defined above;
l°) a $C_2$–$C_7$ alkoxycarbonyl group substituted by a

group wherein R' and R" are as defined above;
each of $R_2$ and $R_3$ is independently;
a) hydrogen, halogen or $C_1$–$C_6$ alkyl;
b) hydroxy, $C_1$—$C_6$ alkoxy or $C_3$ or $C_4$ alkenyloxy; or
c) nitro, amino, formylamino or $C_2$–$C_8$ alkanoylamino;
$R_4$ represents hydrogen or $C_1$–$C_6$ alkyl; and
Q represents hydrogen, carboxy, $C_2$–$C_7$ alkoxycarbonyl or a

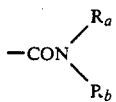

group wherein $R_a$ represents hydrogen or $C_1$–$C_{20}$ alkyl and $R_b$ represents $C_1$–$C_{20}$ alkyl, a

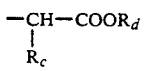

group where $R_c$ and $R_d$ are as defined above or a —$(A)_m$—$R_5$ group wherein m is zero or 1, A is a $C_1$–$C_6$ alkylene chain and $R_5$ is:
a') $C_5$–$C_8$ cycloalkyl;

b') pyridyl, unsubstituted or substituted by one or two substituents chosen independently from halogen, $C_1$-$C_6$ alkyl and $C_1$-$C_6$ alkoxy;

c') phenyl, unsubstituted or substituted by one or two substituents independently chosen from halogen, $CF_3$, $C_1$-$C_6$ alkyl, $C_1$-$C_6$ alkoxy, amino, nitro, formylamino, $C_2$-$C_8$ alkanoylamino, di($C_1$-$C_6$ alkyl)-amino, hydroxy, formyloxy and $C_2$-$C_8$ alkanoyloxy;

d') phenyl substituted by a —$CH_2OH$, COOH, $C_2$-$C_7$ alkoxycarbonyl or a $$-CH_2-N\diagup^{R'}_{\diagdown R''}$$

group wherein R' and R" are as defined above and optionally by another substituent chosen from halogen, $C_1$-$C_6$ alkyl, $C_1$-$C_6$ alkoxy, amino, nitro, formylamino, $C_2$-$C_8$ alkanoylamino, hydroxy, formyloxy and $C_2$-$C_8$ alkanoyloxy, or e') 2-thienyl, 2-furyl or 1-($C_1$-$C_6$ alkyl)-pyrrol-2-yl; or f') a heterocyclic ring which is selected from 2-pyrimidyl, 2-thiazolyl and 3-isoxazolyl and which is unsubstituted or substituted by $C_1$-$C_6$ alkyl;

and the pharmaceutically acceptable salts thereof; and wherein, when $R_1$ is hydrogen, then Q is only a $$-CON\diagup^{R_a}_{\diagdown R_b}$$

group in which $R_a$ is as defined above and either $R_b$ is a $$-CH-COOR_d$$
$$\quad|$$
$$\quad R_c$$

group wherein $R_c$ and $R_d$ are as defined above or $R_b$ is a") a —$(CH_2)_z$—$R'_5$ group wherein z is zero, 1 or 2 and $R'_5$ is as $R_5$ as defined above under d'), e') or f') or b") a $$CH-R_5$$
$$|$$
$$CH_3$$

or —A'—$R_5$ group, wherein A' is a $C_3$-$C_6$ alkylene chain and $R_5$ is as defined above.

The present invention includes within its scope all possible isomers, stereoisomers and optical isomers and their mixtures, and the metabolites and the metabolic precursors or biprecursors of the compounds of formula (I). It has to be noticed that the compounds of formula (I) may be represented also by a tautomeric structure, namely the enol structure of formula (Ia)

(Ia)

wherein
X, R, $R_1$, $R_2$, $R_3$, $R_4$ and Q are as defined above.

However, the compounds of formula (Ia), which fall within the scope of the present invention too, are described in the present specification as compounds of formula (I).

A halogen atom is preferably chlorine or fluorine.

The alkyl, alkylene, alkanoyloxy, alkoxy and alkanoylamino groups may be branched or straight chain groups.

A $C_1$-$C_{20}$ alkyl group is preferably a $C_1$-$C_6$ alkyl group.

A $C_1$-$C_6$ alkyl group is, e.g., methyl, ethyl, propyl, isopropyl, butyl or tert.butyl, more preferably methyl, ethyl or tert.butyl, in particular methyl or ethyl.

A $C_3$ or $C_4$ alkenyloxy group is preferably allyloxy.

A $C_1$-$C_6$ alkoxy group is, e.g., methoxy, ethoxy, propoxy, isopropoxy, butoxy or tert.butoxy, preferably it is methoxy, ethoxy or propoxy.

A di($C_1$-$C_6$ alkyl)-amino is preferably a di($C_1$-$C_4$ alkyl)-amino group, in particular a di($C_1$ or $C_2$ alkyl)-amino one.

A $C_5$-$C_8$ cycloalkyl group is preferably cyclopentyl or cyclohexyl.

A $C_2$-$C_8$ alkanoylamino group is preferably acetylamino or propionylamino.

A $C_2$-$C_8$ alkanoyloxy group is preferably acetoxy or propionyloxy.

A $C_2$-$C_7$ alkoxycarbonyl group is preferably a $C_2$-$C_5$ alkoxycarbonyl group, in particular a $C_2$ or $C_3$ alkoxycarbonyl one.

A $C_1$-$C_6$ alkylene chain is preferably a $C_1$-$C_3$ alkylene chain, such as a —$CH_2$—, —$(CH_2)_2$—, —$(CH_2)_3$—, $$-CH- \quad \text{or} \quad -CH-$$
$$\;|\qquad\qquad\qquad\;|$$
$$\;CH_3\qquad\qquad\;C_2H_5$$

chain.

A $C_3$-$C_6$ alkylene chain is preferably a $C_3$ alkylene chain, in particular a —$(CH_2)_3$— or a $$-CH- \text{ chain.}$$
$$\;|$$
$$\;C_2H_5$$

In a $$-CH-COOR_d$$
$$\quad|$$
$$\quad R_c$$

group, wherein $R_d$ is as defined above and $R_c$ is ad defined above except hydrogen, the asymmetric carbon atom to which —$R_c$ and —$COOR_d$ are linked may have either the R or S configuration. The side-chain of an α-aminoacid is specifically the residue obtained from an α-aminoacid by removing the amino and the carboxy groups together with the α-carbon atom to which they are linked. The side-chain of an αaminoacid as defined above is preferably the side-chain deriving from a naturally occurring aminoacid. Examples of such aminoacids are alanine, valine, leucine, isoleucine, phenylalanine, proline, hydroxyproline, serine, threonine, cysteine, cystine, methionine, tryptophan, tyrosine, asparagine, glutamine, aspartic acid, glutamic acid, lysine, arginine, histidine and phenylserine.

Preferred examples of side chains of the above mentioned aminoacids are —$CH_3$ (deriving from alanine), —$CH_2CH(CH_3)_2$ (deriving from leucine) and —$CH_2C_6H_5$ (deriving from phenylalanine).

Examples of pharmaceutically acceptable salts are either those with inorganic bases, such as sodium, potassium, calcium and aluminium hydroxides, or with organic bases, such as lysine, arginine, N-methylglucamine, triethylamine, triethanolamine, dibenzylamine, methylbenzylamine, di-(2-ethyl-hexyl)-amine, piperidine, N-ethylpiperidine, N,N-diethylaminoethylamine, N-ethyl- morpholine, β-phenethylamine, N-benzyl-β-phenethylamine, N-benzyl-N,N-dimethylamine and the other acceptable organic amines, as well as the salts with inorganic, e.g., hydrochloric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

As stated above, the present invention also includes within its scope pharmaceutically acceptable bioprecursors (otherwise known as prodrugs) of the compounds of formula (I), i.e., compounds which have a different formula to formula (I) above, but which nevertheless upon administration to a human being are converted directly or indirectly in vivo into a compound of formula (I).

Preferred compounds of the invention are the compounds of formula (I), where

X is oxygen or a —$S(O)_p$—group, in which p is zero of 1;

R represents unsubstituted pyridyl or phenyl, unsubstituted or substituted by one or two substituents chosen independently from halogen, trifluoromethyl, $C_1$-$C_4$ alkyl, $C_1$-$C_4$ alkoxy, nitro, amino and $C_2$-$C_8$ alkanoylamino;

$R_1$ is a°°) hydrogen, COOH, CHO, $CH_2OH$, $C_2$-$C_7$ alkoxycarbonyl or a

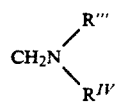

group, wherein each of R''' and $R^{IV}$ independently is $C_1$ or $C_2$ alkyl, or R''' and $R^{IV}$, taken together with the nitrogen atom to which they are linked, form a N-pyrrolidinyl, N-piperazinyl, morpholino or piperidino ring which is unsubstituted or substituted by methyl;

b°°) a

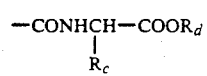

group wherein $R_d$ is hydrogen or $C_1$-$C_6$ alkyl and $R_c$ is hydrogen, phenyl or the side-chain of an α-aminoacid as defined above;

c°°) a

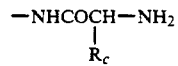

group, wherein $R_c$ is as defined above;

d°°) a —$CH_2OCO(CH_2)_nCOOR_d$ or a —$NHCO(CH_2)_nCOOR_d$ group, wherein n and $R_d$ are as defined above;

e°°) a —$CH=N-OR'_1$ group, wherein $R'_1$ is hydrogen or a —$CH_2COOH$ group;

f°°) a —$CH=N-NHR'_2$ group, wherein $R'_2$ is hydrogen or —$CH_2CH_2OH$;

g°°) a

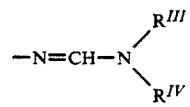

group, wherein $R^{III}$ and $R^{IV}$ are as defined above;

h°°) a $C_2$-$C_4$ alkoxycarbonyl group substituted by a

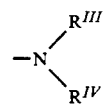

group, wherein $R^{III}$ and $R^{IV}$ are as defined above;

$R_2$ and $R_3$ each independently is hydrogen, halogen, nitro, amino, hydroxy, $C_1$-$C_4$ alkyl or $C_1$-$C_4$ alkoxy;

$R_4$ represents hydrogen or $C_1$-$C_4$ alkyl;

Q represents hydrogen, $C_2$-$C_5$ alkoxycarbonyl or a —$CONR'_aR'_b$ group, wherein $R'_a$ is hydrogen or $C_1$-$C_6$ alkyl and $R'_b$ is $C_1$-$C_6$ alkyl or a

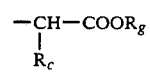

group, wherein $R_g$ is hydrogen or $C_1$-$C_4$ alkyl and $R_c$ is as defined above; or $R'_b$ is a —$(A'')_m$—$R''_5$ group, wherein m is zero or 1, A'' is a $C_1$-$C_3$ alkylene chain and $R''_5$ is:

a''') unsubstituted pyridyl or phenyl, unsubstituted or substituted by one or two substituents chosen independently from halogen, $CF_3$, $C_1$-$C_4$ alkyl, $C_1$-$C_4$ alkoxy, hydroxy, nitro and di-($C_1$-$C_4$ alkyl) amino;

b''') phenyl, substituted by —$CH_2OH$, COOH, or a

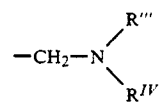

group, wherein R''' and R^IV are as defined above, and optionally by another substituent chosen from C₁-C₄ alkyl, C₁-C₄ alkoxy, hydroxy, formyloxy and C₂-C₆ alkanoyloxy; or c''') 2-thienyl or 2-furyl; or d''') 2-thiazolyl or 3-isoxazolyl, wherein said heterocyclic rings may be unsubstituted or substituted by methyl;

and the pharmaceutically acceptable salts thereof; and wherein, when R₁ is hydrogen, then Q is only a

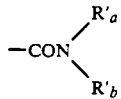

group, wherein R'ₐ is as defined above and R'ᵦ is (1) a

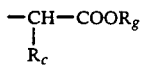

group wherein R_c and R_g are as defined above or (2) a —(CH₂)_z—R''₅ group, wherein z is zero, 1 or 2 and R'''₅ is as R''₅ defined above under b'''), c''') and d'''), or (3) a

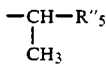

group wherein R''₅ is as defined above.

More preferred compounds of the invention are the compounds of formula (I) wherein X is oxygen or sulphur;

R is phenyl, unsubstituted or substituted by a substituent selected from nitro, halogen, CF₃, C₁-C₄ alkyl and C₁-C₄ alkoxy;

R₁ is a a°°°) hydrogen, —COOH, —CHO, —CH₂OH, C₂-C₅-alkoxycarbonyl, or a

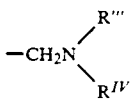

group, wherein R''' and R^IV are as defined above; each of R₂ and R₃ independently is hydrogen, halogen, nitro, amino, hydroxy, C₁-C₄ alkyl or C₁-C₄ alkoxy;

b°°°) a

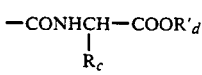

group, wherein R'_d is hydrogen or C₁-C₄ alkyl and R_c is as defined above;

c°°°) a

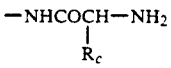

group wherein R_c is as defined above;

d°°°) a —CH₂OOO(CH₂)_n COOR'_d or a —NHOO(CH₂)_n COOR'_d group, wherein n and R'_d are as defined above;

e°°°) a

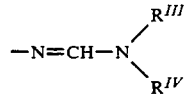

group, wherein R^III and R^IV are as defined above;

f°°°) a C₂-C₄ alkoxycarbonyl group substituted by a

group, wherein R^III and R^IV are as defined above;

R₄ represents hydrogen or methyl; Q represents hydrogen or a —CONR''ₐR''ᵦ group, wherein R''ₐ is hydrogen or C₁-C₄ alkyl and R''ᵦ is C₁-C₄ alkyl or a

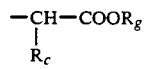

group wherein R_c and R_g are as defined above; or R''ᵦ is a —OCH₂)_z—R₅^IV group, wherein z is zero, 1 or 2 and R^IV₅ is a^IV) unsubstituted pyridyl or phenyl, unsubstituted or substituted by a substituent chosen from nitro, halogen, CF₃, C₁-C₄ alkyl, C₁-C₄ alkoxy and di(C₁-C₂ alkyl)-amino;

b^IV) phenyl, substituted by —CH₂OH, —COOH or a

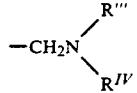

group, wherein R''' and R^IV are as defined above, and optionally by another substituent chosen from hydroxy and C₁-C₄ alkoxy; or c^IV) 2-thienyl or 2-furyl;

d^IV) 2-thiazolyl or 3-isoxazolyl, unsubstituted or substituted by methyl; and the pharmaceutically acceptable salts thereof; and wherein, when R₁ is hydrogen, then Q is a —CONR''ₐR''ᵦ group, wherein R''ₐ is as defined above and R''ᵦ is (1) a

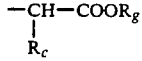

group, wherein R_c and R_g are as defined above; or (2) or —(CH₂)_z—R^V₅ group, wherein z is as defined above and R^V₅ is as R^IV₅ defined above under b^IV), c^IV) or d^IV).

Examples of preferred compounds of the invention are:

N-[2-cyano-3-(1,4-dihydro-1-phenyl-[1]-benzothiopyrano[4,3-c]pyrazol-3-yl]-3-oxo-propanoyl]-glycine, methyl ester;

N-[2-cyano-3-(1,4-dihydro-1-phenyl-[1]-benzothiopyrano[4,3-c]pyrazol-3-yl]- 3-oxo-propanoyl]-DL-leucine, methyl ester;

N-[2-cyano-3-(1,4-dihydro-1-phenyl-[1]-benzothiopyrano[4,3-c]pyrazol-3-yl]-3-oxo-propanyl]-DL-phenylalanine, methyl ester;

N-[2-cyano-3-(1,4-dihydro-1-phenyl-[1]-benzothiopyrano[4,3-c]pyrazol-3-yl]-3-oxo-propanoyl]-DL-phenylglycine, methyl ester;

2-cyano-3-(1,4-dihydro-1-phenyl-[1]-benzothiopyrano[4,3-c]pyrazol-3-yl]-3-oxo-N-(2-thenyl)-propanamide;

2-cyano-N-(2-furfuryl)-3-(1,4-dihydro-1-phenyl-[1]-benzothiopyrano [4,3-c]pyrazol-3-yl)-3-oxo-propanamide;

2-cyano-3-(3-fluoro-1,4-dihydro-6-morpholinomethyl-1-phenyl-[1]-benzopyrano[4,3-c]pyrazol-3-yl)-3-oxo-N-phenyl-propanamide;

2-cyano-3-(1,4-dihydro-8-morpholinomethyl-1-phenyl-[1]-benzopyrano [4,3-c]pyrazol-3-yl)-3-oxo-N-phenyl-propanamide;

2-cyano-3-(1,4-dihydro-1-phenyl-[1]-benzothiopyrano[4,3-c]pyrazol-3-yl)-N-(2-morpholinomethyl-benzyl)-3-oxo-propanamide;

N-[2-cyano-3-(1,4-dihydro-1-phenyl-[1]-benzothiopyrano[4,3-c]pyrazol-3-yl)-3-oxo-propanoyl]-DL-leucine;

2-cyano-3-(8-ethoxycarbonyl-1,4-dihydro-1-phenyl-[1]-benzothiopyrano [4,3-c]pyrazol-3-yl)-3-oxo-N-phenyl-propanamide;

2-cyano-3-(6-ethoxycarbonyl-1,4-dihydro-1-phenyl-[1]-benzothiopyrano [4,3-c]pyrazol-3-yl)-3-oxo-N-phenyl-propanamide;

N-[1,4-dihydro-1-phenyl-3-(2-phenylcarbamoyl-cyanoacetyl)-[1]-benzothiopyrano[4,3-c]pyrazol-8-yl]carbonyl-glycine methyl ester;

N-[1,4-dihydro-1-phenyl-3-(2-phenylcarbamoyl-cyanoacetyl)-[1]-benzothiopyrano[4,3-c]pyrazol-6-yl]carbonyl-glycine methyl ester;

2-cyano-3-(8-ethoxalylamino-1,4-dihydro-1-phenyl-[1]-benzothiopyrano [4,3-c]pyrazol-3-oxo-N-phenyl-propanamide;

2-cyano-3-(1,4-dihydro-8-oxalamino-1-phenyl-[1]-benzothiopyrano[4,3-c]pyrazol-3-yl)-3-oxo-N-phenyl-propanamide;

2-cyano-3-(1,4-dihydro-8-N,N-dimethylaminoethoxycarbonyl-1-phenyl-[1]-benzothiopyrano[4,3-c]pyrazol-3-yl)-3-oxo-N-phenyl-propanamide;

2-cyano-3-(1,4-dihydro-6-N,N-dimethylaminoethoxycarbonyl-1-phenyl-[1]-benzothiopyrano[4,3-c]pyrazol-3-yl)-3-oxo-N-phenyl-propanamide;

and the pharmaceutically acceptable salts thereof, in particular the sodium and the potassium salts.

The compounds of formula (I) and the salts thereof can be prepared by a process comprising;

a) reacting a compound of formula (II)

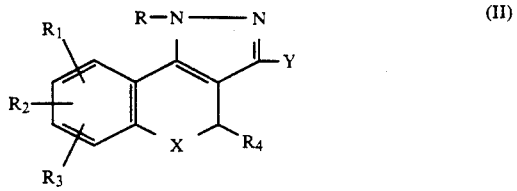

wherein
X, R, $R_1$, $R_2$, $R_3$ and $R_4$ are as defined above and Y is carboxy or a reactive derivative of a carboxy group, with a compound of formula (III)

wherein
Q' is as Q defined above, except carboxy, so obtaining a compound of formula (I), wherein Q is as defined above except carboxy; or b) reacting a compound of formula (IV)

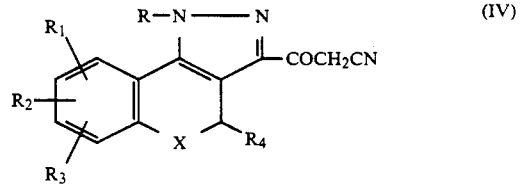

wherein
X, R, $R_1$, $R_2$, $R_3$ and $R_4$ are as defined above, with a compound of formula (V)

wherein
$R_b$ is as defined above, so obtaining a compound of formula (I) wherein Q is a —CONHR$_b$ group, wherein $R_b$ is as defined above; or c) reacting a compound of formula (VI)

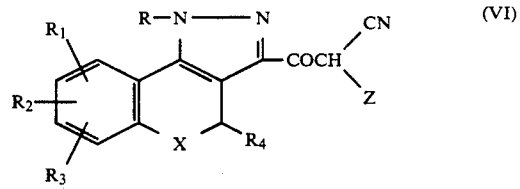

wherein
X, R, $R_1$, $R_2$, $R_3$ and $R_4$ are as defined above and Z is a reactive derivative of a carboxy group, with a compound of formula (VII)

wherein
$R_a$ and $R_b$ are as defined above, so obtaining a compound of formula (I) wherein Q is a

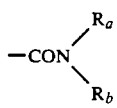

group, wherein $R_a$ and $R_b$ are as defined above; or d) hydrolysing a compound of formula (I), wherein Q is $C_2$-$C_7$ akoxycarbonyl or a

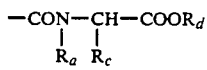

group, in which $R_a$ and $R_c$ are as defined above and $R_d$ is $C_1$-$R_6$ alkyl, so as to obtain the corresponding compound of formula (I), wherein Q is a free carboxy group or a

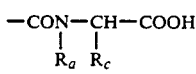

group, in which $R_a$ and $R_c$ are as defined above; and, if desired, converting a compound of formula (I) into another compound of formula (I) and/or, if desired, converting a compound of formula (I) into a pharmaceutically acceptable salt and/or, if desired, converting a salt into a free compound, and/or, if desired, separating a mixture of isomers of a compound of formula (I), into the single isomers.

When Y is a reactive derivative of a carboxy group, it is, for example, a halocarbonyl group, preferably a chlorocarbonyl group, or a $C_2$-$C_7$ alkoxycarbonyl group, preferably a $C_2$ or $C_3$ alkoxycarbonyl group. The reaction between a compound of formula (II) wherein Y is carboxy and a compound of formula (III) may be carried out, for example, in the presence of a condensing agent such as diethyl cyanophosphonate, in the presence of a base such as triethylamine, in an inert solvent such as dimethylformamide at a temperature varying between about 0° C. and about 50° C. The reaction between a compound of formula (II) wherein Y is a reactive derivative of a carboxy group and a compound of formula (III) may be carried out, for example, in the presence of a strong base such as sodium hydride, potassium t.butoxide, thallous ethoxide, in an inert solvent such as 1,2-dimethoxyethane, dioxane, dimethylformamide, at a temperature varying between about 0° C. and about 100° C.

The reaction between a compound of formula (IV) and a compound of formula (V) may be carried out, for example, in the presence of a base such as sodium hydride or triethylamine, in an inert solvent such as toluene, dioxane, tetrahydrofuran, dimethylformamide, at a temperature varying between about 0° C. and about 100° C.

In the compounds of formula (VI), Z is, for example, a halocarbonyl group, preferably a chlorocarbonyl group, or a $C_2$-$C_7$ alkoxycarbonyl group, preferably a $C_2$-$C_3$ alkoxycarbonyl group. The reaction between a compound of formula (VI), where Z is a halocarbonyl group, and a compound of formula (VII) may be carried out, for example, in an inert solvent such as dichloroethane, dioxane, dimethylformamide, in the presence of pyridine or triethylamine as acid acceptor, at a temperature varying between about 0° C. and about 100° C.

The reaction between a compound of formula (VI), where Z is $C_1$-$C_6$ alkyl ester, and a compound of formula (VII) may be carried out, for example, by heating at the reflux temperature in an aromatic hydrocarbon such as toluene or xylene, preferably distilling off slowly together with the diluent the free $C_1$-$C_6$ alkyl alcohol generated during the reaction.

Hydrolysis of a compound of formula (I), wherein Q is a $C_2$-$C_7$ alkoxycarbonyl group or a

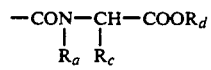

group in which $R_a$ and $R_c$ are as defined above and $R_d$ is $C_1$-$C_6$ alkyl, according to process-variant d) above, may be performed by selective basic hydrolysis, using e.g. aqueous sodium or potassium hydroxide in a solvent such as ethanol or dimethylformamide, at a temperature varying between about 0° C. and about 80° C.

A compound of formula (I) may be converted, as stated above, into another compound of formula (I) by known methods; for example, in a compound of formula (I) a nitro group may be converted into an amino group by treatment, for example, with stannour chloride in concentrated hydrochloric acid, using, if necessary, an organic cosolvent such as acetic acid, dioxane, tetrahydrofuran, at a temperature varying between room temperature and about 100° C. Furthermore, for example, an amino group may be converted into a formylamino or a $C_2$-$C_8$ alkanoylamino group, for example by reacting with formic acid or with the suitable $C_2$-$C_8$ alkanoyl anhydride, without any solvent or in an organic solvent such as dioxane, dimethylformamide, tetrahydrofuran, usually in the presence of a base such as pyridine or triethylamine, at a temperature varying between 0° C. and about 100° C. Furthermore, for example, a —NH$_2$ or a —CH=N—NH$_2$ group may be converted into a

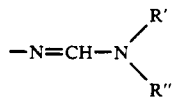

group or into a

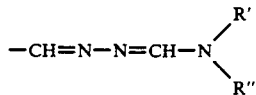

group, wherein R' and R'' are as defined above, respectively, by reaction with a quaternary nitrogen compound of formula (VIIa)

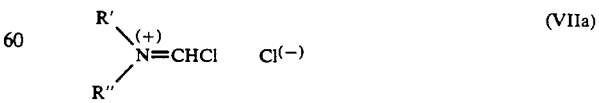

wherein R' and R'' are as defined above, in an organic inert solvent, such as dioxane, tetrahydrofuran, chloroform, dichloromethane, 1,2-dichloroethane, benzene or toluene, in the presence of a tertiary amine, such as triethylamine, at a temperature varying between about −20° C. and room temperature, according to the experimental procedure described in GB-A-1,293,590 and in U.S. Pat. No. 4,447,432. Furthermore, for example, an amino group may be converted into a $$-\text{NHCOCHNH}_2 \\ \phantom{-\text{NHCOCH}}| \\ \phantom{-\text{NHCOCH}}R_c$$

group, wherein $R_c$ is as defined above, by reaction with a suitably protected α-aminoacid of formula $$\text{HOOC}-\text{CH}-\text{NHE}, \\ \phantom{\text{HOOC}-}| \\ \phantom{\text{HOOC}-}R_c$$

wherein $R_c$ is as defined above and E is a protective group, such as a benzyloxycarbonyl or a tert-butoxycarbonyl group, in the presence of dicyclohexylcarbodiimide as condensing agent, in an inert organic solvent such as dioxane, tetrahydrofuran or acetonitrile, at a temperature varying between about 0° C. and room temperature, so as to obtain the protected $$-\text{NHCOCHNHE} \\ \phantom{-\text{NHCOCH}}| \\ \phantom{-\text{NHCOCH}}R_c$$

group, wherein $R_c$ and E are as defined above, which in turn is deprotected using well known methods in organic chemistry. Furthermore, for example, a carboxy group may be converted into a $$-\text{CONHCHCOOH} \\ \phantom{-\text{CONH}}| \\ \phantom{-\text{CONH}}R_c$$

group, wherein $R_c$ is as defined above, by reaction with an esterified α-aminoacid of formula $$\text{H}_2\text{N}-\text{CH}-\text{COOR}'_d, \\ \phantom{\text{H}_2\text{N}-}| \\ \phantom{\text{H}_2\text{N}-}R_c$$

wherein $R'_d$ is $C_1-C_6$ alkyl and $R_c$ is as defined above, in the presence of dicyclohexylcarbodiimide as condensing agent, in an inert organic solvent such as dioxane, tetrahydrofuran or acetonitrile, at a temperature varying between about 0° c. and room temperature, so as to obtain the esterified $$-\text{CONHCH}-\text{COOR}'_d \\ \phantom{-\text{CONH}}| \\ \phantom{-\text{CONH}}R_c$$

group, wherein $R_c$ and $R'_d$ are as defined above, which in turn is hydrolyzed to give the $$-\text{CONHCH}-\text{COOH} \\ \phantom{-\text{CONH}}| \\ \phantom{-\text{CONH}}R_c$$

group, wherein $R_c$ is as defined above, following methods well known in the art, for example, those described for the process variant d) above. Furthermore, for example, an alkoxycarbonyl group, a $$-\text{CH}_2\overset{\overset{\displaystyle O}{\|}}{P}\!\!\begin{array}{l}\diagup OR'_d \\ \diagdown OR'_d\end{array}$$

group, a $-\text{CH}_2\text{OCO}(\text{CH}_2)_n\text{COOR}'_d$ group or a $-\text{NHCO}(\text{CH}_2)_n\text{COOR}'_d$ group, wherein n and $R'_d$ are as defined above, may be converted into the corresponding $-\text{COOH}$, $$-\text{CH}_2\overset{\overset{\displaystyle O}{\|}}{P}\!\!\begin{array}{l}\diagup OH \\ \diagdown OH'\end{array}$$

$-\text{CH}_2\text{OCO}(\text{CH}_2)_n\text{COOH}$ and $-\text{NHCO}(\text{CH}_2)_n\text{COOH}$ group, respectively, wherein n is as defined above, by treatment with aqueous sodium or potassium hydroxide in a solvent such as dioxane, methanol, ethanol or dimethylformamide, at a temperature varying between about 0° C. and about 80° C. The optional esterification of a free carboxy group as well as the optional conversion of a carboxylic ester into the free carboxy derivative may be carried out according to known methods in organic chemistry.

Process-variants b) and c) described above may be considered as examples of conversions of a compound of formula (I) into another compound of formula (I) too. Also the optional salification of a compound of formula (I) as well as the conversion of a salt into the free compound and the separation of a mixture of isomers into the single isomers may be carried out by conventional methods.

For example, the separation of optical isomers may be carried out by salification with an optically active base or acid and by subsequent fractional crystallization of the diastereoisomeric salts, followed by recovery of the optically active isomeric acids or, respectively, bases.

The compounds of formula (II), wherein Y is a $C_2-C_7$ alkoxycarbonyl group, may be prepared, according to the methods described in EP-A-274443, for example, by reacting a compound of formula (VIII)

$$\text{(VIII)}$$

wherein
X, $R_1$, $R_2$, $R_3$ and $R_4$ are as defined above and $R_6$ is $C_1-C_6$ alkyl, preferably $C_1-C_2$ alkyl, with a compound of formula (IX)

$$R-\text{NHNH}_2 \qquad \text{(IX)}$$

wherein
R is as defined above.

The reaction between a compound of formula (VIII) and a compound of formula (IX) may be carried out, for example, in a solvent such as $C_1-C_6$ alkyl alcohol, dioxane, tetrahydrofuran, dimethylformamide, acetic acid, at a temperature varying between about 0° C. and about 150° C.

The compounds of formula (II), wherein Y is carboxy may be prepared, for example, by hydrolysis of the corresponding compounds of formula (II) wherein Y is $C_2$–$C_7$ alkoxycarbonyl, according to standard methods well known in the art, for example, by basic hydrolysis, carried out e.g. by treatment with sodium or potassium hydroxide in a solvent such as water, $C_1$–$C_6$ alkyl alcohol, dioxane, dimethylformamide and their mixtures, at a temperature varying between about 0° C. and about 80° C. The compounds of formula (II), wherein Y is halocarbonyl, preferably chlorocarbonyl, may be prepared, for example, by reaction of the corresponding compound of formula (II), wherein Y is carboxy, with a suitable acid halide, for example oxalyl chloride, thionyl chloride, $PCl_3$, $PBr_3$, in an inert solvent such as ether, benzene, dichloroethane, dioxane or without any solvent, at a temperature varying between about 0° C. and about 100° C.

The compounds of formula (III) are, in some cases, commercially available products, or may be prepared by methods well known in the art. For example, a compound of formula (III), wherein Q is a

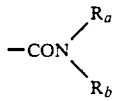

group, wherein $R_a$ and $R_b$ are as defined above, may be prepared by reacting cyanoacetic acid with a compound of formula (VII) in the presence of a condensing agent such as dicyclohexylcarbodiimide, 1,1-carbonyldiimidazole and the like, in an inert organic solvent such as benzene, dioxane, acetonitrile, at a temperature varying between about 0° C. and about 50° C.

The compounds of formula (IV) are compounds of general formula (I), wherein Q is hydrogen and may be obtained by process a) above, for example, by reacting a compound of formula (II), wherein Y is $C_2$–$C_7$ alkoxycarbonyl, with acetonitrile, in the presence of a strong base e.g., sodium hydride, potassium tert-butoxide, in an inert organic solvent such as benzene, dioxane, tetrahydrofuran, at a temperature varying between about 0° C. and about 100° C.

The compounds of formula (VI), wherein Z is $C_2$–$C_7$ alkoxycarbonyl, are compounds of general formula (I) wherein Q is $C_2$–$C_7$ alkoxycarbonyl and may be obtained by process a) above, for example, by reacting a compound of formula (II) with a compound of formula (X)

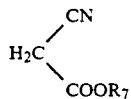

wherein
$R_7$ is $C_1$–$C_6$ alkyl, using the same experimental conditions as described above for the reaction between a compound of formula (II) and a compound of formula (III).

The compounds of formula (IV), wherein Z is halocarbonyl, may be prepared, for example, by basic hydrolysis of a compound of formula (VI), wherein Z is $C_2$–$C_7$ alkoxycarbonyl, using, for example, the same experimental conditions described above for the hydrolysis of the compounds of formula (II), wherein Y is $C_2$–$C_7$ alkoxycarbonyl, in order to obtain the corresponding carboxy derivative, which in turn may be transformed into a compound of formula (VI), wherein Z is halocarbonyl, preferably chlorocarbonyl, using, for example, the same experimental conditions described above for the preparation of the compounds of formula (II), wherein Y is halocarbonyl.

The compounds of formula (VIII) may be prepared, for example, by reacting a compound of formula (XI)

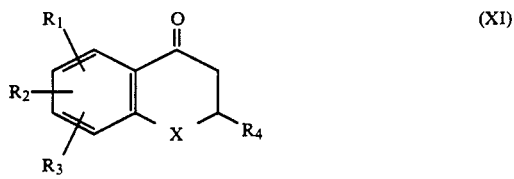

wherein
X, $R_1$, $R_2$, $R_3$ and $R_4$ are as defined above, with a compound of formula (XII)

wherein
each of $R_8$ and $R'_8$, being the same or different, is $C_1$–$C_6$ alkyl, preferably methyl or ethyl.

The reaction between a compound of formula (XI) and a compound of formula (XII) may be carried out, for example, in the presence of a strong base such as sodium methoxide, sodium ethoxide, sodium hydride, potassium tert.butoxide, in an organic solvent such as $C_1$–$C_6$ alkyl alcohol, benzene, dioxane, dimethylformamide, at a temperature varying between about 0° C. and about 100° C.

The compounds of formula (XI) may be prepared by synthetic methods well known in the art, for example, according to the methods described in J.A.C.S. 76, 5065 (1954) and in "Advances in Heterocyclic Chemistry", 18, 59 (1975).

The compounds of formula (V), (VII), (IX), (X) and (XII) are known products and may be prepared by conventional methods: in some cases they are commercially available products.

When in the compounds of the present invention and in the intermediate products thereof, groups are present, such as COOH, $NH_2$, CHO and/or OH, which need to be protected before submitting them to the reactions described above, they may be protected before the reactions take place and then deprotected, according to well known methods in organic chemistry.

The compounds of formula (I) possess immunomodulating activity and can be used, for example, as immunostimulating agents e.g., in the treatment of acute and chronic infections of both bacterial and viral origin, alone or in association with antibiotic agents, and in the treatment of neoplastic diseases, alone or in association with antitumoral agent, in mammals.

The immunomodulating activity of the compounds of the invention is proved, for example, by the fact that they are effective in potentiating the cytotoxic activity of the macrophages towards tumour cells in vitro.

The experimental procedure to evaluate this activity is as follows: groups of 4 mice are treated i.p. with the tested compounds and then, seven days later, peritoneal cells are collected and plated for 2 hours at 37° C. After this period the walls are washed to eliminate the non adherent cells, tumour target cells are then added and the incubation is prolonged for 48 hours. At the end of this period the target cells viability is evaluated by a colorimetric method and quantified at 570 nm.

The compounds of the invention can be safely used in medicine by virtue of their negligible toxicity.

The therapeutic regiment for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute infections. For the maintenance regimens the oral or parenteral, e.g., intramuscular or subcataneous, route is preferred.

For the purposes the compounds of the invention can be administered orally at doses ranging e.g., from about 0.5 to about 10 mg/kg of body weight per day in adult humans.

Doses of active compounds ranging e.g., from about 0.2 to about 5 mg/kg of body weight can be used for parenteral administration in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspension, tablets, pills, gelatine capsules, syrups, drops or suppositories. Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulsoe, carboxymethylcellulose, gum-arabic, tragacanth, polyvinylpyrrolidone; disaggregating agents, such as starches, alginic acid, alginates, sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g., syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g., sterile water, olive oil, ethyl oleate, glycols, e.g., propylene glycol, and if desired, a suitable amount of licodaine hydrochloride.

The solutions for intravenous injections or infusions may contain as carrier, for example, sterile water or preferably they may be in the form of sterile aqueous isotonic saline solutions. The suppositions may contain together with the active compound a pharmaceutically acceptable carrier, e.g., cocoa-butter, polyethylene glycol, a polyoxyethylene sorbitan fatty acid ester surfactant or lecithin.

The following examples illustrate but do not limit the invention:

EXAMPLE 1

1,4-Dihydro-1-phenyl-[1]-benzothiopyrano[4,3-c]pyrazole-3-carboxylic acid (2 g) is reacted with thionyl chloride (1 ml) in dioxane (40 ml) at reflux temperature for 2 hours. After cooling the solution is evaporated to dryness in vacuo to give 1,4-dihydro-1-phenyl-[1]-benzothiopyrano[4,3-c]pyrazole-3-carbonyl chloride as crystalline residue. The crude product is dissolved in anhydrous dioxane (15 ml) and reacted for 2 h under stirring at room temperature with the carbanion obtained by treatment of cyanacetic acid, 2-morpholinomethylbenzylamide (1.95 g) with 50% sodium hydride (0.39 g) in anhydrous dioxane/dimethylformamide 9:1 (20 ml) at room temperature.

The reaction mixture is then diluted with ice water and acidified to pH 3 with citric acid. The precipitation is filtered and dissolved in $CHCl_3$. The organic solution is washed with 2% citric acid solution and then with water. Evaporation to dryness in vacuo gives a residue which is purified over a flash column using chloroform/methanol 10:0.5 as eluent. Final crystallization from chloroform/methanol yields 1.1 g of
2-cyano-3-(1,4-dihydro-1-phenyl-[1]-benzothiopyrano[4,3-c]pyrazol-3-yl)-N-(2-morpholinomethylbenzyl)-3-oxo-propanamide, m.p. 243°–245° C.

By proceeding analogously the following compounds can be prepared:

2-cyano-3-(1,4-dihydro-1-phenyl-[1]-benzothiopyrano[4,3-c]pyrazol-3-yl)-N-(3-morpholinomethylbenzyl)-3-oxo-propanamide, mp. 150° C. dec.;

2-cyano-3-(1,4-dihydro-1-phenyl-[1]-benzothiopyrano[4,3-c]-pyrazol-3-yl)-N-(3-dimethylaminomethyl-benzyl)-3-oxo-propanamide;

2-cyano-3-(1,4-dihydro-1-phenyl-[1]-benzothiopyrano[4,3-c]pyrazol-3-yl)-N-(2-methoxy-3-morpholinomethylbenzyl)-3-oxopropanamide;

2-cyano-3-(1,4-dihydro-1-phenyl-[1]-benzothiopyrano[4,3-c]pyrazol-3-yl)-N-(4-methoxy-3-morpholinomethylbenzyl)-3-oxopropanamide;

2-cyano-3-(1,4-dihydro-1-phenyl-[1]-benzothiopyrano[4,3-c]pyrazol-3-yl)-N-[2-(4-methyl-piperazin-1-yl)methyl-benzyl]3-oxo-propanamide;

2-cyano-3-(1,4-dihydro-1-phenyl-[1]-benzothiopyrano[4,3-c]pyrazol-3-yl)-3-oxo-N-[2-(pyrrolidin-1-yl)methyl-benzyl]propanamide;

2-cyano-3-(1,4-dihydro-1-phenyl-[1]-benzothiopyrano[4,3-c]pyrazol-3-yl)-N-(2-morpholinomethylphenyl)-3-oxo-propanamide;

2-cyano-3-(1,4-dihydro-1-phenyl-[1]-benzothiopyrano[4,3-c]pyrazol-3-yl)-N-(3-morpholinomethylphenyl)-3-oxo-propanamide;

2-cyano-3-(1,4-dihydro-1-phenyl-[1]-benzothiopyrano[4,3-c]pyrazol-3-yl)-N-(3-dimethylaminomethyl-phenyl)-3-oxo-propanamide;

2-cyano-3-(1,4-dihydro-1-phenyl-[1]-benzothiopyrano[4,3-c]pyrazol-3-yl)-N-(2,dimethylaminomethyl-phenyl)-3-oxo-propanamide;
2-cyano-3-(1,4-dihydro-1-phenyl-[1]-benzothiopyrano[4,3-c]pyrazol-3-yl)-N-(2-methoxy-3-morpholinomethylphenyl)-3-oxo-propanamide;
2-cyano-3-(1,4-dihydro-1-phenyl-[1]-benzothiopyrano[4,3-c]pyrazol-3-yl)-N-(2,hydroxy-3-morpholinomethyl-phenyl)-3-oxo-propanamide;
2-cyano-3-(1,4-dihydro-1-phenyl-[1]-benzothiopyrano[4,3-c]pyrazol-3-yl)-N-(4-methoxy-3-morpholinomethylphenyl)-3-oxopropanamide;
2-cyano-3-(1,4-dihydro-1-phenyl-[1]-benzothiopyrano[4,3-c]pyrazol-3-yl)-N-(3-hydroxy-4-hydroxymethyl-phenyl)-3-oxopropanamide; and
2-cyano-3-(1,4-dihydro-1-phenyl-[1]-benzothiopyrano[4,3-c]pyrazol-3-yl)-N-(3-hydroxy-4-hydroxymethyl-benzyl)-3-oxopropanamide.

EXAMPLE 2

By proceeding according to Example 1, by reaction with suitable cyanacetamides, the following compounds can be prepared:
2-cyano-N-(2-furfuryl)-3-(1,4-dihydro-1-phenyl-[1]-benzothiopyrano[4,3-c]pyrazol-3-yl)-3-oxo-propanamide, m.p. 236°–238° C.;
2-cyano-3-(1,4-dihydro-1-phenyl-[1]-benzothiopyrano[4,3-c]pyrazol-3-yl)-3-oxo-N-(2-thenyl)-propanamide;
2-cyano-3-(1,4-dihydro-1-phenyl-[1]-enzothiopyrano[4,3-c]pyrazol-3-yl)-N-[2-(1-methyl-pyrrol-2-yl)-ethyl]-3-oxo-propanamide, m.p. 171°–176° C.;
2-cyano-3-(1,4-dihydro-1-phenyl-[1]-benzothiopyrano[4,3-c]pyrazol-3-yl)-3-oxo-N-(2-thiazolyl)-propanamide;
2-cyano-3-(1,4-dihydro-1-phenyl-[1]-benzothiopyrano[4,3-c]pyrazol-3-yl)-N-(3-isoxazolyl)-3-oxo-propanamide; and
2-cyano-3-(1,4-dihydro-1-phenyl-[1]-benzothiopyrano[4,3-c]pyrazol-3-yl)-3-oxo-N-(1-phenylethyl)-propanamide, m.p. 228°–230° C.

EXAMPLE 3

By proceeding to Example 2, starting from suitable substituted 1,4-dihydro-[1]-benzopyrano[4,3-c]pyrazole-3-carboxylic acids the following compounds can be prepared:
2-cyano-3-(8-fluoro-1,4-dihydro-6-morpholinomethyl-1-phenyl-[1]-benzopyrano[4,3-c]pyrazol-3-yl)-3-oxo-N-phenyl-propanamide, m.p. 249°–253°;
2-cyano-3-(1,4-dihydro-8-morpholinomethyl-1-phenyl-[1]-benzopyrano [4,3-c]pyrazol-3-yl)-3-oxo-N-phenyl-propanamide, m.p. 200°–210° C. dec;
2-cyano-3-(3-fluoro-1,4-dihydro-6-dimethylaminomethyl-1-phenyl-[1]-benzopyrano[4,3-c]pyrazol-3-yl)-3-oxo-N-phenyl-propanamide;
2-cyano-3-[8-fluoro-1,4-dihydro-6-(4-methyl-piperazin-1-yl)-1-phenyl[1]-benzopyrano[4,3-c]pyrazol-3-yl]-3-oxo-N-phenyl-propanamide;
2-cyano-3-[8-fluoro-1,4-dihydro-1-phenyl-6-(pyrrolidin-1-yl)-[1]-benzopyrano[4,3-c]pyrazol-3-yl]-3-oxo-N-phenyl-propanamide;
2-cyano-3-[1,4-dihydro-8-(4-methyl-piperazin-1-yl)-1-phenyl-[1]-benzopyrano[4,3-c]pyrazol-3-yl]-3-oxo-N-phenyl-propanamide;
2-cyano-3-[1,4-dihydro-1-phenyl-8-(pyrrolidin-1-yl)-[1]-benzopyrano [4,3-c]pyrazol-3-yl]-3-oxo-N-phenyl-propanamide;
N-benzyl-2-cyano-3-(8-fluoro-1,4-dihydro-6-morpholinomethyl-1-phenyl-[1]-benzopyrano[4,3-c]pyrazol-3-yl)-3-oxo-propanamide;
N-benzyl-2-cyano-3-(1,4-dihydro-8-morpholinomethyl-1-phenyl-[1]-benzopyrano[4,3-c]pyrazol-3-yl)-3-oxo-propanamide;
2-cyano-N-(4-fluoro-phenyl)-3-(1,4-dihydro-8-morpholinomethyl-1-phenyl-[1]-benzopyrano[4,3-c]pyrazol-3-yl)-3-oxo-propanamide; and
N-(3-chloro-phenyl)-2-cyano-3-(1,4-dihydro-8-morpholinomethyl-1-phenyl-[1]-benzopyrano[4,3-c]pyrazol-3-yl)-3-oxo-propanamide.

EXAMPLE 4

1,4-dihydro-1-phenyl-[1]-benzothiopyrano[4,3-c]pyrazole-3-carboxylic acid, ethyl ester (3,2 g) is heated with 1% KOH solution in ethanol (80 ml) under reflux for 30 minutes. The reaction mixture is diluted with ice water and acidified to pH 3 with 37% HCl. The precipitate is filtered, washed with water and dried in vacuo at 50° C. to give 1,4-dihydro-1-phenyl-[1]-benzothiopyrano[4,3-c]pyrazol-3-carboxylic acid (2.6 g) which is reacted with thionyl chloride (0.9 ml) in dioxane (50 ml) under reflux for 2 hours. After cooling, the solution is evaporated to dryness in vacuo to give 1,4-dihydro-1-phenyl-[1]-benzothiopyrano[4,3-c]pyrazol-3-carbonyl chloride as a crystalline residue. The crude product is dissolved in anhydrous dioxane (35 ml) and reacted for 1 hour under stirring at room temperature with the carbanion obtained by treatment of N-cyanoacetylglycine, methyl ester (1.44 ng) with 50% sodium hydride (0.54 g) in anhydrous dimethylformamide/dioxane 1:1 (30 ml) at room temperature. The reaction mixture is then diluted with ice water and acidified to pH 2 with N HCl. The precipitate is filtered and dissolved in ethyl acetate, then the organic solution is washed with N HCl and then with water until neutral. Evaporation to dryness yields a residue which is purified over a Flash column using chloroform/methanol/30% NH$_4$OH 80:20:0.5 as eluent. Final treatment with acetone of the purified fractions gives 1.65 g of N-[2-cyano-3-(1,4-dihydro-1-phenyl-[1]-benzothiopyrano[4,3-c]pyrazol-3-yl)-3-oxopropanoyl]-glycine,-methyl ester, m.p. 208°–210° C., NMR (CDCl$_3$) δppm: 3.81(s) (3H, —COOCH$_3$), 4.18 (d) (2H, —CONHCH$_2$—), 4.21(s) (2H, —S—CH$_2$—), 6.82(t) (1H, —CONHCH$_2$), 6.85-7.7 (m) (9H, phenyl protons), 16.32(s) (1H, —OH).

The proceeding analogously the following compounds can be prepared:
N-[2-cyano-3-(1,4-dihydro-1-phenyl-[1]-benzothiopyrano[4,3-c]pyrazol-3-yl)-3-oxo-propanoyl]-DL-leucine, methyl ester, m.p. 115°–125° C.;
N-[2-cyano-3-(1,4-dihydro-1-phenyl-[1]-benzothiopyrano[4,3-c]pyrazol-3-yl)-3-oxo-propanoyl]-DL-phenylglycine, methyl ester, m.p. 180°–182° C.;
N-[2-cyano-3-(1,4-dihydro-1-phenyl-[1]-benzothiopyrano[4,3-c]pyrazol-3-yl)-3-oxo-propanoyl]-DL-phenylalanine, methyl ester; and
N-[2-cyano-3-(1,4-dihydro-1-phenyl-[1]-benzothiopyrano[4,3-c]pyrazol-3-yl)-3-oxo-propanoyl]-DL-isoleucine, methyl ester.

Similarly the pure D and L enantiomers of the above-listed compounds can be prepared.

EXAMPLE 5

N-[2-cyano-3-(1,4-dihydro-1-phenyl-[1]-benzothiopyrano[4,3-pyrazol-3-yl)-3-oxo-propanoyl]-glycine, methyl ester (1.9 g), is suspended in 1% KOH solution in 95% ethanol (61 ml) and heated under stirring under reflux for 30 minutes. After cooling the precipitate is filtered and washed with ethanol, then dissolved in water. The aqueous basic solution is extracted with ethyl acetate and then acidified to pH 2 with 2N HCl. The precipitate is extracted with ethyl acetate and the organic solution washed with N HCl and then with water until neutral. Evaporation to dryness in vacuo gives a residue which is crumbled with ethanol to yield 1.35 g of N-[2-cyano-3-(1,4-dihydro-1-phenyl-[1]-benzothiopyrano[4,3-c]pyrazol-3-yl)-3-oxo-propanoyl]-glycine, m.p. 224°-226° C., NMR (DMSO d6) δppm: 3.94(s) (2H, —CONHCH$_2$—), 4.19(s) (2H, —S—CH$_2$), 6.8–7.7(m) (9H, phenyl protons).

By proceeding analogously the following compounds can be prepared:

N-[2-cyano-3-(1,4-dihydro-1-phenyl-[1]-benzothiopyrano[4,3-c]pyrazol-3-yl)-3-oxo-propanoyl]-DL-leucine, m.p. 220°-222° C.;

N-[2-cyano-3-(1,4-dihydro-1-phenyl-[1]-benzothiopyrano[4,3-c]pyrazol-3-yl)-3-oxo-propanoyl]-DL-phenylalanine;

N-[2-cyano-3-(1,4-dihydro-1-phenyl-[1]-benzothiopyrano[4,3-c]pyrazol-3-yl)-3-oxo-propanoyl]-DL-phenylglycine, m.p. 210°-213° C.; and N-[2-cyano-3-(1,4-dihydro-1-phenyl-[1]-benzothiopyrano[4,3-c]pyrazol-3-yl)-3-oxo-propanoyl]-DL-isoleucine.

Similarly the pure D and L enantiomers of the above-listed compounds can be obtained.

EXAMPLE 6

8-fluoro-1,4-dihydro6-morpholinomethyl-1-phenyl-[1]-benzopyrano[4,3-c]pyrazole-3-carboxylic acid, ethyl ester (5.6 g) is reacted with acetonitrile (15 ml) in dioxane (15 ml) in the presence of 50% sodium hydride (0.6 g) under stirring at 60° C. for 30 minutes. After cooling the reaction mixture is diluted with ice water and acidified to pH 3 with citric acid. The precipitate is extracted with ethyl acetate and the organic phase washed with water until neutral and then evaporated to dryness in vacuo. The residue is purified over a SiO$_2$ column using chloroform/methanol 95:5 as eluent to give 2.4 g of 3-(8-fluoro-1,4-dihydro-6-morpholinomethyl-1-phenyl-[1]-benzopyrano[4,3-c]pyrazol-3-yl)-3-oxo-propanenitrile, m.p. 187°-189° C.

By proceeding analogously the following compound can be prepared; 3-(1,4-dihydro-8-morpholinomethyl-1-phenyl-[1]-benzopyrano[4,3-c]pyrazol-3-yl)-3-oxo-propanenitrile, m.p. 189°-190° C.

EXAMPLE 7

3-(8-fluoro-1,4-dihydro-6-morpholinomethyl-1-phenyl-[1]-benzopyrano[4,3-c]pyrazol-3-yl)-3-oxo-propanenitrile (2.8 g) is reacted with phenylisocyanate (0.8 g) in dimethylformamide (20 ml) in the presence of triethylamine (0.7 g) at 25°-30° C. for 30 min. The reaction mixture is diluted with ice water and acidified with citric acid to pH 3. The precipitate is filtered and dissolved in chloroform. The organic solution is washed with 2% citric acid solution and then with water until neutral. Evaporation to dryness in vacuo gives a residue which is crystallized from chloroform/ethanol to yield 1.9 g of 2-cyano-3-(8-fluoro-1,4-dihydro-6-morpholinomethyl-1-phenyl-[1]-benzopyrano[4,3-c]pyrazol-3-yl)-3-oxo-N-phenyl-propanamide, m.p. 249°-253° C.

By proceeding analogously the following compound can be prepared:
2-cyano-3-(1,4-dihydro-8-morpholinomethyl-1-phenyl-[1]-benzopyrano[4,3-c]pyrazol-3-yl)-3-oxo-N-phenyl-propanamide, m.p. 200°-210° C. dec.

EXAMPLE 8

2,3-Dihydro-4-oxo-4H-[1]-benzothiopyran-6-carboxylic acid, m.p. 223°-225° C. (40.5 g) is reacted with thionyl chloride (46.3 g) in anhydrous dioxane (810 ml) at reflux temperature for 4 hours. After cooling the solution is evaporated to dryness in vacuo and the residue of crude 2,3-dihydro-4-oxo-4H-[1]-benzothiopyran-6-carbonyl chloride is dissolved in anhydrous benzene (600 ml). This solution is added under nitrogen at room temperature to a stirred mixture of anhydrous tert-.butanol (300 ml) in benzene (500 ml) and pyridine (470 ml). The reaction mixture is allowed to react for 20 hours at room temperature and then is evaporated to dryness in vacuo. The residue is dissolved in ethyl acetate and the organic solution is washed with 5% citric acid solution, then with water until neutral and finally evaporated to dryness in vacuo. The residue is purified over a SiO$_2$ column using hexane/ethyl acetate 90/10 as eluent.

The recovered product is treated with hexane under stirring to give 2,3-dihydro-4-oxo-4H-[1]-benzothiopyran-6-carboxylic acid, tert-butyl ester, m.p. 125°-127° C. (34.5 g), which is reacted with diethyl oxalate (83.8 g) in anhydrous ethanol (1000 ml) in the presence of sodium ethoxide (31 g) under stirring at room temperature for 2 hours. The reaction mixture is diluted with ice water and acidified to pH 4 with citric acid. The precipitate is filtered, washed with water and then dissolved in ethyl acetate. The organic solution is evaporated to dryness in vacuo to yield 3-ethoxalyl-2,3-dihydro-4-oxo-4H-[1]-benzothiopyran-6-carboxylic acid, tert-butyl ester (45 g), which is reacted with phenylhydrazine (16 g) in acetic acid (1660 ml) at 25°-30° C. for 90 minutes. The reaction mixture is diluted with ice water and the precipitate is filtered, dissolved in chloroform and washed with water. After evaporation of the solvent in vacuo, the residue is purified by treatment with isopropyl ether under stirring to yield 8-tert-butoxycarbonyl-1,4-dihydro-1-phenyl-[1]-benzothiopyrano[4,3-c]pyrazole-3-carboxylic acid, ethyl ester, m.p. 146°-149° C. (27.5 g), which is hydrolyzed by treatment with potassium hydroxide (5.3 g) in 95% ethanol (1200 ml) under stirring at room temperature for 20 hours. The reaction mixture is diluted with ice water and acidified to pH 4 with citric acid. The precipitate is filtered, washed with water until neutral and dried in vacuo at 80° C. to give 8-tert-butoxycarbonyl-1,4-dihydro-1-phenyl-[1]-benzothiopyrano[4,3-c]pyrazole-3-carboxylic acid, m.p. 295°-297° C. (23.9 g) which is dissolved in anhydrous dioxane (1000 ml) and reacted with oxalyl chloride (16.3 g) in the presence of a catalytic amount of dimethylformamide (70 mg) at room temperature for 4 hours. The reaction mixture if evaporated to dryness in vacuo and the residue, 8-tert-butoxycarbonyl-1,4-dihydro-1-phenyl-[1]-benzothiopyrano[3,4-c]pyrazole-3-carbonyl chloride (24.8 g), is dissolved in anhydrous dioxane (980 ml) and added under stirring to the suspension obtained by treatment of cyanoacetanilide (10.28 g) with 50% sodium hydride (3.75 g) in anhydrous dioxane (1230 ml) at room temperature. The reaction mixture is kept under stirring at room temperature for 1 hour and then diluted with ice water and acidified to pH 3 with 2N HCl. The precipitate is filtered and dissolved in ethyl acetate, the organic solution is washed with 1N HCl and then with water until neutral. Evaporation to dryness in vacuo gives a residue which is purified by treatment with ethanol under reflux. After cooling the precipitate is filtered and washed with ethanol to yield 3-(8-tert-butoxycarbonyl-1,4-dihydro-1-phenyl-[1]-benzothiopyrano [4,3-c]pyrazol-3-yl)-2-cyano-3-oxo-N-phenyl-propanamide, m.p. 229°–230° C. (12.8 g), which is reacted with trifluoroacetic acid (128 ml) under stirring at room temperature for 1 hour. The reaction mixture is diluted with ethanol (128 ml) and the precipitate is filtered and washed with ethanol to yield 11.3 g of 3-(8-carboxy-1,4-dihydro-1-phenyl-[1]-benzothiopyrano[4,3-c]pyrazol-3-yl)-2-cyano-3-oxo-N-phenyl-propanamide, m.p. 284°–287° C.

By proceeding analogously the following compounds can be prepared:
3-(6-carboxy-1,4-dihydro-1-phenyl-[1]-benzothiopyrano[4,3-c]pyrazol-3-yl)-2-cyano-3-oxo-N-phenyl-propanamide, m.p. 283°–287° C.;
3-(8-carboxy-1,4-dihydro-1-phenyl-[1]-benzopyrano[4,3-c]pyrazol-3-yl)-2-cyano-3-oxo-N-phenyl-propanamide; and
3-(6-carboxy-1,4-dihydro-1-phenyl[1]-benzothiopyrano[4,3-c]pyrazol-3-yl)-2-cyano-N-(4-fluoro-phenyl)-3-oxo-propanamide.

EXAMPLE 9

3-(8-Carboxy-1,4-dihydro-1-phenyl-[1]-benzothiopyrano[4,3-c]pyrazol-3-yl)-2-cyano-3-oxo-N-phenyl-propanamide (0.65 g) dissolved in dimethylformamide (50 ml) is reacted with methyl iodide (0.37 g) in the presence of anhydrous potassium carbonate (0.36 g) under stirring at room temperature for 2 hours. The reaction mixture is diluted with ice water and the precipitate is filtered, dissolved in chloroform and washed with 1N HCl and then with water. Evaporation of the solvent in vacuo gives a residue which is crystallized from CH$_2$Cl$_2$/methanol to yield 0.48 g of 2-cyano-3-(1,4-dihydro-8-methoxycarbonyl-1-phenyl-[1]-benzothiopyrano[4,3-c]pyrazol-3-yl)-3-oxo-N-phenyl-propanamide, m.p. 228°–230° C.

By proceeding analogously the following compounds can be prepared:
2-cyano-3-(8-ethoxycarbonyl-1,4-dihydro1-phenyl-[1]-benzothiopyrano[4,3-c]pyrazol-3-yl)-3-oxo-N-phenyl-propanamide, m.p. 241°–242° C.;
2-cyano-3-(6-ethoxycarbonyl-1,4-dihydro-1-phenyl-[1]-benzothiopyrano[4,3-c]pyrazol-3-yl)-3-oxo-N-phenyl-propanamide, m.p. 263°–264° C.;
N-(3-chloro-phenyl)-2-cyano-3-(6-ethoxycarbonyl-1,4-dihydro-1-phenyl-[1]-benzothiopyrano[4,3-c]pyrazol-3-yl)-3-oxo-propanamide;
2-cyano-3-(6-ethoxycarbonyl-1,4-dihydro-1-phenyl-[1]-benzothiopyrano[4,3-c]pyrazol-3-yl)-N-(4-fluoro-phenyl)-3-oxopropanamide;
2-cyano-3-(6-ethoxycarbonyl-1,4-dihydro-1-phenyl-[1]-benzothiopyrano[4,3-c]pyrazol-3-yl)-3-oxo-N-(3-trifluoromethylphenyl)-3-oxo-propanamide;
2-cyano-3-[6-ethoxycarbonyl-1-(4-fluoro-phenyl)-1,4-dihydro-[1]-benzothiopyrano[4,3-c]pyrazol-3-yl]-3-oxo-N-phenyl-propanamide; and
2-cyano-3-(8-ethoxycarbonyl-1,4-dihydro-1-phenyl-[1]benzopyrano[4,3-c]pyrazol-3-yl)-3-oxo-N-phenyl-propanamide.

EXAMPLE 10

Glycine methyl ester hydrochloride (0.7 g) suspended in anhydrous acetonitrile (250 ml) is treated with triethylamine (0.56 g) under stirring at room temperature. To the suspension first 3-(8-carboxy-1,4-dihydro-1-phenyl-[1]-benzothiopyrano[ 4,3-c]pyrazol-3-yl)-2-cyano-3-oxo-N-phenyl-propanamide (2.5 g) and then dicyclohexylcarbodiimide (1.25 g) are added. The reaction mixture is kept under stirring at room temperature for 4 hours and then is basified to pH 8 by adding dimethylaminoethanol. The precipitate is filtered, washed with acetonitrile and then eliminated. The organic solution is concentrated in vacuo to a small volume, diluted with water, acidified to pH 2 with 1N HCl and finally basified to pH 8 with 1N NaOH. The obtained precipitate is filtered, washed with water, dissolved in chloroform and washed with 1N HCl and then with water until neutral. The organic solution is evaporated in vacuo to dryness and the residue is purified over a SiO$_2$ column using chloroform/methanol 90/10 as eluent. Final crystallization from CH$_2$Cl$_2$/ethyl acetate yields 1.48 g of N-[1,4-dihydro-1-phenyl-3-(2-phenylcarbamoyl-cyanoacetyl)-[1]-benzothiopyrano[4,3-c]pyrazol-8-yl[carbonyl glycine methyl ester, m.p. 253°–256° C.

By proceeding analogously the following compounds can be prepared:
N-[1,4-dihydro-1-phenyl-3-(2-phenylcarbamoyl-cyanoacetyl)[1]-benzothiopyrano[4,3-c]pyrazol-6-yl]carbonyl-glycine methyl ester, m.p. 268°–273° C. dec;
N-[1,4-dihydro-1-phenyl-3-(2-phenylcarbamoyl-cyanoacetyl)[1]-benzothiopyrano[4,3-c]pyrazol-8-yl]carbonyl-L-alanine methyl ester;
N-[1,4-dihydro-1-phenyl-3-(2-phenylcarbamoyl-cyanoacetyl)-[1]-benzothiopyrano[4,3-c]pyrazol-6-yl]carbonyl-L-alanine methyl ester;
N-[1,4-dihydro-1-phenyl-3-(2-phenylcarbamoyl-cyanoacetyl)[1]-benzothiopyrano[4,3-c]pyrazol-8-yl]carbonyl-L-leucine methyl ester;
N-[1,4-dihydro-1-phenyl-3-(2-phenylcarbamoyl-cyanoacetyl)[1]-benzothiopyrano[4,3-c]pyrazol-6-yl]carbonyl-L-leucine methyl ester;
N-[1,4-dihydro-1-phenyl-3-(2-phenylcarbamoyl-cyanoacetyl)[1]-benzothiopyrano[4,3-c]pyrazol-6-yl]-carbonyl-L-phenylalanine methyl ester; and
N-{3-[2-(4-fluorophenylcarbamoyl)-cyanoacetyl]-1,4-dihydro-1-phenyl-[1]-benzothiopyrano[4,3-c]pyrazol-8-yl}carbonylglycine methyl ester.

EXAMPLE 11

N-[1,4-Dihydro-1-phenyl-3-(2-phenylcarbamoyl-cyanoacetyl([1]-benzothiopyrano[4,3-c]pyrazol-8-yl]carbonyl-glycine methyl ester (0.8 g) is suspended in 1% KOH solution in 95% ethanol (22.3 ml) and heated under stirring at the reflux temperature for 30 minutes. After cooling the reaction mixture is acidified to pH 2 with 23% HCl and the diluted with ice water. The precipitate is filtered, washed with water and then crystallized from CHCl$_3$/ethanol to yield 0.73 g of N-[1,4-dihydro-1-phenyl-3-(2-phenylcarbamoylcyanoacetyl)-[1]-benzothiopyrano[4,3-c]pyrazol-8-yl]carbonyl glycine, m.p. 244°–250° C.

By proceeding analogously the following compounds can be prepared:
N-[1,4-dihydro-1-phenyl-3-(2-phenylcarbamoyl-cyanoacetyl)[1]-benzothiopyrano[4,3-c]pyrazol-6-yl]carbonyl-glycine;

N-[1,4-dihydro-1-phenyl-3-(2-phenylcarbamoyl-cyanoacetyl)[1]-benzothiopyrano[4,3-c]pyrazol-8-yl]carbonyl-L-alanine;

N-[1,4-dihydro-1-phenyl-3-(2-phenylcarbamoyl-cyanoacetyl)[1]-benzothiopyrano[4,3-c]pyrazol-6-yl]carbonyl-L-alanine;

N-[1,4-dihydro-1-phenyl-3-(2-phenylcarbamoyl-cyanoacetyl)[1]-benzothiopyrano[4,3-c]pyrazol-8-yl]carbonyl-L-leucine;

N-[1,4-dihydro-1-phenyl-3-(2-phenylcarbamoyl-cyanoacetyl)[1]-benzothiopyrano[4,3-c]pyrazol-6-yl]carbonyl-L-leucine; and N-[1,4-dihydro-1-phenyl-3-(2-phenylcarbamoyl-cyanoacetyl)[1]-benzothiopyrano[4,3-c]pyrazol-6-yl]carbonyl-L-phenylalanine.

EXAMPLE 12

3-(8-amino-1,4-dihydro-1-phenyl-[1]-benzothiopyrano[4,3-c]pyrazol-3-yl)-2-cyano-3-oxo-N-phenyl-propanamide (1.1 g) dissolved in anhydrous tetrahydrofuran (23 ml) is reacted with succinic anhydride (0.71 g) at the reflux temperature under stirring for 3 hours. After cooling the reaction mixture is diluted with ice water. The precipitate is filtered and washed with water. Crystallization from CHCl₃/methanol yields 0.9 g of 3-[8-(3-carboxy-propanoylamino)-1,4-dihydro-1-phenyl-[1]-benzothiopyrano[4,3-c]pyrazol-3-yl]-2-cyano-3-oxo-N-phenylpropanamide, m.p. 230°–233° C.

By proceeding analogously the following compounds can be prepared:

3-[6-(3-carboxy-propanoylamino)-1,4-dihydro-1-phenyl-[1]-benzothiopyrano[4,3-c]pyrazol-3-yl]-2-cyano-3-oxo-N-phenylpropanamide;

3-[8-(2-carboxy-acetylamino)-1,4-dihydro-1-phenyl-[1]-benzothiopyrano[4,3-c]pyrazol-3-yl]-2-cyano-3-oxo-N-phenyl-propanamide; and 3-[3-(3-carboxy-propanoylamino)-1,4-dihydro-1-phenyl-[1]-benzopyrano[4,3-c]pyrazol-3-yl]-2-cyano-3-oxo-N-phenyl-propanamide.

EXAMPLE 13

3-(3-Amino-1,4-dihydro-1-phenyl-[1]-benzothiopyrano[4,3-c]pyrazol-3-yl)-2-cyano-3-oxo-N-phenyl-propanamide (1.2 g) dissolved in anhydrous dimethylformamide (70 ml) containing pyridine (1 ml) is reacted with ethyl oxalyl chloride (0.7 g) under stirring at room temperature for 6 hours. The reaction mixture is diluted with ice water and acidified to pH 4 with citric acid. The precipitate is filtered and washed with water. Crystallization from CHCl₃/ethanol yields 1.2 g of 2-cyano-3-(8-ethoxalylamino-1,4-dihydro-1-phenyl-[1]-benzothiopyrano[4,3-c]pyrazol-3-yl)-3-oxo-N-phenyl-propanamide, m.p. 273°–277° C.

By proceeding analogously the following compounds can be prepared:

2-cyano-3-(6-ethoxalylamino-1,4-dihydro-1-phenyl-[1]-benzothiopyrano[4,3-c]pyrazol-3-yl)-3-oxo-N-phenyl-propanamide;

2-cyano-3-(8-ethoxalylamino-1,4-dihydro-1-phenyl-[1]-benzothiopyrano[4,3-c]pyrazol-3-yl)-N-(4-fluoro-phenyl)-3-oxopropanamide;

N-(3-chloro-phenyl)-2-cyano-3-(8-ethoxalylamino-1,4-dihydro-1-phenyl-[1]-benzothiopyrano[4,3-c]pyrazol-3-yl)-3-oxo-propanamide;

2-cyano-3-(8-ethoxalylamino-1,4-dihydro-1-phenyl-[1]-benzothiopyrano[4,3-c]pyrazol-3-yl)-N-(3-nitro-phenyl)-3-oxopropanamide;

2-cyano-3-(8-ethoxalylamino-1,4-dihydro-1-phenyl-[1]-benzothiopyrano[4,3-c]pyrazol-3-yl)-3-oxo-N-(3-trifluoromethylphenyl)-propanamide; and 2-cyano-3-[8-ethoxalylamino-1-(4-fluoro-phenyl)-1,4-dihydro[1]-benzothiopyrano[4,3-c]pyrazol-3-yl]-3-oxo-N-phenyl-propanamide.

EXAMPLE 14

2-Cyano-3-(8-ethoxalylamino-1,4-dihydro-1-phenyl-[1]-benzothiopyrano[4,3-c]pyrazol-3-yl)-3-oxo-N-phenyl-propanamide (1.1 g) is treated with 1% KOH solution in 95% ethanol (28.6 ml) diluted with 95% ethanol (50 ml) under stirring at room temperature for 3 hours. The reaction mixture is concentrated in vacuo to a small volume and then diluted with ice water and acidified to pH 4 with citric acid. The precipitate is filtered and washed with water. Crystallization from CHCl₃/ethanol yields 0.7 g of 2-cyano-3-(1,4-dihydro-8-oxalamino-1-phenyl-[1]-benzothiopyrano[4,3-c]pyrazol-3-yl)-3-oxo-N-phenyl-propanamide, m.p. 236°–242° C. dec.

By proceeding analogously the following compounds can be prepared:

2-cyano-3-(1,4-dihydro-6-oxalamino-1-phenyl-[1]-benzothiopyrano[4,3-c]pyrazol-3-yl)-3-oxo-N-phenyl-propanamide;

2-cyano-N-(4-fluoro-phenyl)-3-(1,4-dihydro-8-oxalamino-1-phenyl-[1]-benzothiopyrano[4,3-c]pyrazol-3-yl)-3-oxo-propanamide;

N-(3-chloro-phenyl)-2-cyano-3-(1,4-dihydro-8-oxalamino-1-phenyl-[1]-benzothiopyrano[4,3-c]pyrazol-3-yl)-3-oxo-propanamide;

2-cyano-3-[1-(4-fluoro-phenyl)-1,4-dihydro-8-oxalamino-1-phenyl-[1]-benzothiopyrano[4,3-c]pyrazol-3-yl]-3-oxo-propanamide; and 2-cyano-3-(1,4-dihydro-8-oxalamino-1-phenyl-[1]-benzopyrano [4,3-c]pyrazol-3-yl)-3-oxo-N-phenyl-propanamide.

EXAMPLE 15

8-Tert-butoxycarbonyl-1,4-dihydro-1-phenyl-[1]-benzothiopyrano [4,3-c]pyrazole-3-carboxylic acid ethyl ester (11.9 g), prepared according to Example 8, is treated under stirring with trifluoroacetic acid (132 ml) at room temperature for 3 hours. The reaction mixture is diluted with ice water and the precipitate is filtered and washed with water until neutral. Crystallization from isopropanol yields 3-ethoxycarbonyl-1,4-dihydro-1-phenyl-[1]-benzothiopyrano[4,3-c]pyrazole-8-carboxylic acid, m.p. 222°–225° C. (9.2 g), which is reacted with thionyl chloride (5.3 ml) in anhydrous dioxane (90 ml) at the reflux temperature for 2 hours. After cooling, the solution is evaporated to dryness in vacuo and the residue, 3-ethoxycarbonyl-1,4-dihydro-1-phenyl-[1]-benzothiopyrano [4,3-c]pyrazole-8-carbonyl chloride, is dissolved in anhydrous diglyme (100 ml) and added dropwise, under inert atmosphere, to a stirred solution of lithium tri-tert-butoxyaluminum hydride (15.4 g) in anhydrous diglyme (90 ml) in such a way as to maintain the temperature between 9° C. and 4° C. The reaction mixture is allowed to react at about 0° C. under stirring for 1 hour and then is diluted with ice water, acidified to pH 1 with 23% HCl and extracted with chloroform. The organic solution is washed with water and then evaporated to dryness in vacuo. The residue is purified over a SiO₂ column using hexane/ethyl acetate 7/3 as eluent, Crystallization from CH₂Cl₂/isopropyl ether yields pure 1,4-dihydro-8-hydroxymethyl-1-phenyl-[1]- benzothiopyrano[4,3-c]pyrazole-3-carboxylic acid ethyl ester, m.p. 160°–162° C. (4.2 g), which is reacted with 2-methoxyethoxymethyl chloride (2.13 g) in methylene chloride (60 ml) in the presence of diisopropylethylamine (2.96 ml) at room temperature for 20 hours. The reaction mixture is washed in a separatory funnel first with 5% Na₂HPO₄ solution and then with water until neutral. The organic phase is evaporated to dryness in vacuo and the residue is crystallized from isopropyl ether to yield 1,4-dihydro-8-(2-methoxyethoxymethoxy)methyl-1-phenyl-[1]-benzothiopyrano[4,3-c]pyrazole-3-carboxylic acid ethyl ester, m.p. 66°–68° C. (5 g), which is treated with KOH (0.4 g) in 95% ethanol (52 ml) under stirring at 45° C. for 40 minutes. The reaction mixture is then diluted with ice water and acidified to pH 4 with citric acid. The precipitate is filtered, washed with water until neutral and dried in vacuo at 80° C. to yield 1,4-dihydro-8-(2-methoxyethoxymethoxy)-methyl-1-phenyl-[1]-benzothiopyrano[4,3-c]pyrazol-3-carboxylic acid, m.p. 136°–139° C. (4.26 g), which is dissolved in anhydrous dioxane (50 ml) and reacted with oxalyl chloride (1.9 ml) in the presence of dimethylformamide (11 mg) at room temperature for 1 hour. The reaction mixture is evaporated to dryness in vacuo and the residue, crude 1,4-dihydro-8-(2-methoxyethoxymethoxy)methyl-1-phenyl-[1]-benzothiopyrano[4,3-c]pyrazole-3-carbonyl chloride, is dissolved in anhydrous dioxane (50 ml) and reacted for 1 hour under stirring at room temperature with the carbanion obtained by treatment of cyano-acetanilide (1.76 g) with 50% sodium hydride (0.6 g) in anhydrous dioxane (140 ml). The reaction mixture is then diluted with ice water and acidified to pH 3 with 2N HCl.

The precipitate is filtered, washed with water and crystallized from CH₂Cl₂/isopropanol to yield 2-cyano-3-[1,4]-dihydro-8-(2-methoxyethoxymethoxy)methyl-1-phenyl-[1]-benzothiopyrano [4,3-c]pyrazol-3-yl]-3-oxo-N-phenyl-propanamide, m.p. 150°–153° C. (1.6 g), which is suspended under stirring in methanol (800 ml) containing 37% HCl (8 ml) and heated at 45° C. for 20 hours. After cooling the reaction mixture is concentrated in vacuo to a small volume and diluted with ice water. The precipitate is filtered and washed with water until neutral. Crystallization from CH₂Cl₂/methanol yields 1.1 g of 2-cyano-3-(1,4-dihydro-8-hydromethyl-1-phenyl-[1]-benzothio-pyrano[4,3-c]pyrazol-3-yl)-3-oxo-N-phenylpropanamide, m.p. 153°–158° C. dec.

By proceeding analogously the following compounds can be prepared:

2-cyano-3-(1,4-dihydro-6-hydroxymethyl-1-phenyl-[1]-benzopyrano [4,3-c]-pyrazol-3-yl)-3-oxo-N-phenyl-propanamide;

2-cyano-3-(1,4-dihydro-8-hydroxymethyl-1-phenyl-[1]-benzopyrano[4,3-c]pyrazol-3-yl)-3-oxo-N-propanamide;

2-cyano-N-(4-fluorophenyl)-3-(1,4-dihydro-8-hydroxymethyl-1-phenyl-[1]benzothiopyrano[4,3-c]-pyrazol-3-yl)-3-oxo-propanamide; and N-(3-chloro-phenyl)-2-cyano-3-(1,4-dihydro-8-hydroxymethyl-1-phenyl-[1]-benzothiopyrano[4,3-c]pyrazol-3-yl)-3-oxo-propanamide.

EXAMPLE 16

3-(8-Carboxy-1,4-dihydro-1-phenyl-[1]-benzothiopyrano[4,3-c]pyrazol-3-yl)-2-cyano-3-oxo-N-phenyl-propanamide (1.35 g) dissolved in anhydrous acetonitrile (110 ml) is reacted with N,N-dimethylaminoethanol (0.73 g), in the presence of dicyclohexylcarbodiimide (1.12 g) and 4-dimethylaminopyridine (0.265 g), under stirring at room temperature for 24 hours. The precipitate is filtered off and the organic solution is concentrated in vacuo to a small volume. The residue is diluted with with water, acidified to pH 2 with NHCl and then basified to pH 8 with N NaOH. The precipitate is filtered and purified over a SiO₂ column using chloroform/methanol/30% NH₄OH 80/20/0.3 as eluent. The recovered product is dissolved in dimethylformamide (20 ml), acidified to pH 2 with 2N HCl, diluted with water (50 ml), and then basified to pH 8 with 2N NaOH. The precipitate is filtered and washed with water to yield 0.4 g of 2-cyano-3-(1,4-dihydro-8-N,N-dimethyl-aminoethoxycarbonyl-1-phenyl-[1]-benzothiopyrano[4,3-c]pyrazol-3-yl)-3-oxo-N-phenyl-propanamide, m.p. 217°–220° C.

By proceeding analogously the following compounds can be prepared:

2-cyano-3-(1,4-dihydro-6-N,N-dimethylaminoethoxycarbonyl-1-phenyl-[1]-benzothiopyrano[4,3-c]pyrazol-3-yl)-3-oxo-N-phenyl-propanamide, m.p. 210°–217° C. dec.;

2-cyano-3-(1,4-dihydro-8-morpholinoethoxycarbonyl-1-phenyl-[1]-benzothiopyrano[4,3-c]pyrazol-3-yl)-3-oxo-N-phenyl-propanamide; and 2-cyano-3-(8-N,N-diethylaminopropoxycarbonyl-1,4-dihydro-1-phenyl-[1]-benzothiopyrano[4,3-c]pyrazol-3-yl)-3-oxo-N-phenyl-propanamide.

EXAMPLE 17

N-Formylmorpholine (7.58 g) dissolved in anhydrous ethyl ether (200 ml) is reacted with oxalyl chloride (8.02 g) under stirring at room temperature for 20 hours. The precipitate is filtered, washed with anhydrous ethyl ether and dried in vacuo at room temperature for 1 hour to yield 8.9 g of 4-chloromethylene-morpholinium chloride. This compound (5.47 g) is added portionwise at −15°60 C. to a stirred solution of 3-(8-amino-1,4-dihydro-1-phenyl-[1]-benzothiopyrano[4,3-c]pyrazol-3-yl)-2-cyano-3-oxo-N-phenyl-propanamide (3 g) in anhydrous tetrahydrofuran (130 ml) containing triethylamine (8.96 ml). The reaction mixture is kept under stirring at −15° C. for 2 hours and then at about 0° C. for 2 hours again. Finally it is diluted with ice water and acidified to pH 4 with citric acid. The precipitate is filtered, fired in vacuo at 50° C. and then purified over a SiO₂ column using chloroform/methanol30% NH₄OH 85/12/0.5 as eluent. The recovered product is crystallized from methanol to yield 1.4 g of 2-cyano-3(1,4-dihydro-8-morpholinomethyleneamino-1-phenyl-[1]-benzothiopyrano[4,3-c]pyrazol-3-yl)-3-oxo-N-phenyl-propanamide, m.p. 205°–210° C.

By proceeding analogously the following compounds can be prepared:

2-cyano-3-(1,4-dihydro-6-morpholinomethyleneamino-1-phenyl-[1]-benzothiopyrano[4,3-c]pyrazol-3-yl)-3-oxo-N-phenyl-propanamide;

2-cyano-3-(1,4-dihydro-1-phenyl-8-piperidinomethyleneamino-[1]-benzothiopyrano[4,3-c]-pyrazol-3-yl)-3-oxo-N-phenylpropanamide; and 2-cyano-3-(1,4-dihydro-8-dimethylaminomethyleneamino-1-phenyl-[1]-benzothiopyrano[4,3-c]pyrazol-3-yl)-3-oxo-N-phenyl-propanamide.

EXAMPLE 18

3-(8-Amino-1,4-dihydro-1-phenyl-[1]-benzothiopyrano[4,3-c]pyrazol-3-yl)-2-cyano-3-oxo-N-phenyl-propanamide (1 g) dissolved in anhydrous acetonitrile (10 ml) is reacted with N-tert-butoxy-carbonylglycine (0.41 g) in the presence of dicyclohexylcarbodiimide (0.53 g) under stirring at room temperature for 2 hours. The precipitate is filtered, washed with acetonitrile and then eliminated. The organic solution is evaporated in vacuo to dryness and the residue is extracted with ethyl acetate (2×100 ml). The insoluble residue is filtered off and the clear organic solution is evaporated in vacuo to dryness. The crude product is purified over a flash column using chloroform/methanol/acetic acid 85/15/0.5 as eluent. The recovered product is crystallized from chloroform-ethyl acetate to yield 3-[8-(N-tert-butoxycarbonylglycyl)amino-1,4-dihydro-1-phenyl-[1]-benzothiopyrano[4,3-c]pyrazol-3-yl]-2-cyano-3-oxo-N-phenylpropanamide, m.p. 190°-200° C. (0.36 g), which is suspended in ethyl acetate containing gaseous HCl (about 2.5 N solution) and kept under stirring at room temperature for 4 hours. The precipitate is filtered, washed with ethyl acetate, suspended in water and treated with 15% NH4OH until pH 8. The suspension is kept under stirring at room temperature and then the precipitate is filtered and washed with water. Purification with methanol at the reflux temperature yields 0.2 g of 2-cyano-3-(8-glycylamino-1,4-dihydro-1-phenyl-[1]-benzothiopyrano[4,3-c]pyrazol-3-yl)-3-oxo-N-phenyl-propanamide, m.p. 218°-221° C.

By proceeding analogously the following compounds can be prepared:

2-cyano-3-(6-glycylamino-1,4-dihydro-1-phenyl-[1]-benzothiopyrano[4,3-c]-pyrazol-3-yl)-3-oxo-N-phenyl-propanamide; and 3-(8-L-alanylamino-1,4-dihydro-1-phenyl-[1]-benzothiopyrano [4,3-c]pyrazol-3-yl)-3-oxo-N-phenyl-propanamide.

EXAMPLE 19

2-Cyano-3-(1,4-dihydro-6-hydroxymethyl-1-phenyl-[1]-benzothiopyrano[4,3-c]pyrazol-3-yl)-3-oxo-N-phenyl-propanamide (1.2 g) is reacted with succinic anhydride (0.8 g) in anhydrous pyridine (40 ml) under stirring at 45° C. for 20 hours. After cooling the reaction mixture is diluted in ice water and the precipitate is filtered and washed with water. Crystallization from CH2Cl2/isopropanol yields 0.95 g of 3-[6-(3-carboxy-propanoyloxymethyl)-1,4-dihydro-1-phenyl-[1]-benzothiopyrano[4,3-c]pyrazol-3-yl]-2-cyano-3-oxo-N-phenyl-propanamide.

By proceeding analogously the following compounds can be prepared:

2-[8-(3-carboxy-propanoyloxymethyl)-1,4-dihydro-1-phenyl-[1]-benzothiopyrano[4,3-c]pyrazol-3-yl]-2-cyano-3-oxo-N-phenyl-propanamide.

EXAMPLE 20

N-[2-cyano-3-(1,4-dihydro-1-phenyl-[1]-benzothiopyrano[4,3-c]pyrazol-3-yl)-3-oxo-propanoyl]-glycine, methyl ester is dissolved by treatment with the stoichiometric amount of sodium ethoxide in ethanol. The solution is evaporated to dryness in vacuo and the product is crumbled with acetone. Filtration and washing with acetone yields the pure sodium salt of N-[2-cyano-3-(1,4-dihydro-1-phenyl-[1]-benzothiopyrano[4,3-c]pyrazol-3-yl)-3-oxo-propanoyl]-glycine, methyl ester, m.p. >260° C.

EXAMPLE 21

Tablets, each weighing 150 mg and containing 50 mg of active substance, can be manufactured as follows:

| Composition (for 10.000 tablets) | |
|---|---|
| N-[2-cyano-3-(1,4-dihydro-1-phenyl-[1]-benzothiopyrano[4,3-c]pyrazol-3-yl)-3-oxo-propanoyl]-glycine, methyl ester | 500 g |
| Lactose | 710 g |
| Corn starch | 238 g |
| Talc powder | 36 g |
| Magnesium stearate | 16 g |

N-[2-cyano-3-(1,4-dihydro-1-phenyl-[1]-benzothiopyrano[4,3-c]pyrazol-3-yl)-3-oxo-propanoyl]-glycine, methyl ester and half of the corn starch are mixed, the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

We claim:

1. A compound formula (I):

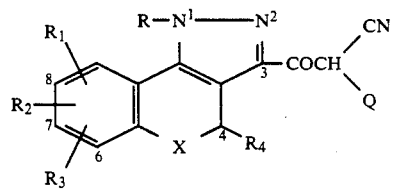

wherein

X represents oxygen or sulphur;

R represents $C_1$-$C_6$ alkyl, pyridyl or phenyl, the phenyl being unsubstituted or substituted by one or two substituents selected from the group consisting of halogen, $CF_3$, $C_1$-$C_6$ alkyl and $C_1$-$C_6$ alkoxy;

$R_1$ is a

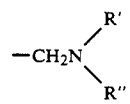

group wherein R' and R'', taken together with the nitrogen atom to which they are linked, form a heterocyclic ring which is selected from the group consisting of N-pyrrolidinyl, N-piperazinyl, thiomorpholino, morpholino and piperidino and which is unsubstituted or substituted by $C_1$-$C_6$ alkyl; or $R_1$ is a

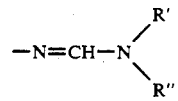

group wherein R' and R'' are as defined above; each of $R_2$ and $R_3$ is, independently hydrogen, halogen, hydroxy, $C_1$-$C_6$ alkyl, $C_1$-$C_6$ alkoxy or $C_3$-$C_4$ alkenyloxy; $R_4$ represents hydrogen or $C_1$-$C_6$ alkyl; and Q represents hydrogen or a

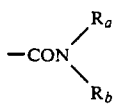

group wherein $R_a$ represents hydrogen or $C_1-C_{20}$ alkyl and $R_b$ represents a $-(A)_m-R_5$ group wherein m is zero or 1, A is a $C_1-C_6$ alkylene chain and $R_5$ is (a) phenyl, unsubstituted or substituted by one or two substituents, independently selected from the group consisting of halogen, $CF_3$, $C_1-C_6$ alkyl, $C_1-C_6$ alkoxy and nitro; or (b) 2-furyl or 2-thienyl; or a pharmaceutically acceptable salt thereof.

2. A compound according to claim 1 selected from the group consisting of: 2-cyano-3-(8-fluoro-1,4-dihydro-6-morpholinomethyl-1-phenyl-[1]-benzopyrano[4,3-pyrazol-3-yl)-3-oxo-N-phenyl-propanamide; 2-cyano-3-(1,4-dihydro-8-morpholinomethyl-1-phenyl-[1]-benzopyrano[4,3-c]pyrazol-3-oxo-N-phenyl-propanamide; N-benzyl-2-cyano-3-(8-fluoro-1,4-dihydro-6-morpholinomethyl-1-phenyl-[1]-benzopyrano[4,3-c]pyrazol-3-yl)-3-oxo-propanamide; and the pharmaceutically acceptable salts thereof.

3. A pharmaceutical composition comprising a pharmaceutically acceptable carrier and/or diluent and, as an active principle, a therapeutically effective amount of a compound of formula (I), or a pharmaceutically acceptable salt thereof, as claimed in claim 1.

4. A method of treating a human or animal patient in need of treatment with an immunostimulating agent, the method comprising administering to said patient a therapeutically effective immunostimulating amount of a compound of formula (I) or salt thereof as claimed in claim 1.

5. A method according to claim 4 for the treatment of an acute or chronic infection of bacterial or viral origin.

6. A method according to claim 4 for the treatment of a neoplastic disease.

* * * * *

UNITED STATES PATENT AND TRADEMARK OFFICE
CERTIFICATE OF CORRECTION

PATENT NO. : 5,166,152
DATED : November 24, 1992
INVENTOR(S) : Gianfederico DORIA et al It is certified that error appears in the above-identified patent and that said Letters Patent is hereby corrected as shown below:

On the title page, Item [22], delete "Jun. 20, 1989" and substitute therefor -- Jun. 16, 1989 --.

Signed and Sealed this

Ninth Day of November, 1993

Attest:

BRUCE LEHMAN

*Attesting Officer*      *Commissioner of Patents and Trademarks*